United States Patent
Hancke et al.

[11] Patent Number: 5,601,533
[45] Date of Patent: Feb. 11, 1997

[54] ENDOSCOPIC PUNCTURE NEEDLE DEVICE

[75] Inventors: Søren Hancke, Hellerup; Peter Vilmann, Copenhagen, both of Denmark

[73] Assignee: GIP Medizin Technik GmbH, Grassau, Germany

[21] Appl. No.: 468,354

[22] Filed: Jun. 6, 1995

[51] Int. Cl.⁶ .................................................. A61M 5/00
[52] U.S. Cl. .......................................... 604/164; 128/753
[58] Field of Search ............................. 604/22, 165, 171, 604/164, 280, 282; 128/753

[56] References Cited

U.S. PATENT DOCUMENTS

| | | | |
|---|---|---|---|
| 3,506,007 | 4/1970 | Henkin | 604/165 X |
| 3,727,613 | 4/1973 | Sorenson et al. | 604/165 |
| 3,766,916 | 10/1973 | Moorehead et al. | 604/165 |
| 3,769,975 | 11/1973 | Nimoy et al. | 604/165 |
| 4,230,123 | 10/1980 | Hawkins et al. | 604/165 X |
| 4,231,367 | 11/1980 | Rash | 604/165 |
| 4,249,541 | 2/1981 | Pratt | 604/165 X |
| 4,445,893 | 5/1984 | Bodicky | 604/165 |
| 5,226,910 | 7/1993 | Kajiyama et al. | 604/22 X |
| 5,342,394 | 8/1994 | Matsuno et al. | 604/22 X |
| 5,480,388 | 1/1996 | Zadini et al. | 604/165 |

*Primary Examiner*—Sam Rimell
*Attorney, Agent, or Firm*—Finnegan, Henderson, Farabow, Garrett, and Dunner

[57] ABSTRACT

An endoscopic puncture needle device comprising: an elastic catheter introducible into an instrument channel of an endoscope; a flexible hollow puncture needle extending through the catheter; a cylindrical handle casing extending in the longitudinal direction of the hollow puncture needle, the proximal end of the catheter being connected to the distal end of the casing; and a hollow rod connected to the proximal end of the hollow puncture needle, for reciprocating the hollow puncture needle within the catheter, said hollow rod being mounted in the handle casing coaxially with the proximal end of the catheter and displaceably in the longitudinal direction. In order to allow for easy and precise adjustment of the puncture depth of the hollow needle arranged in the catheter of the puncture needle device, the distal end portion of the handle casing is provided with a thread which can be screwed to a threaded hollow pipe socket arranged at the entry of the instrument channel of the endoscope.

8 Claims, 1 Drawing Sheet

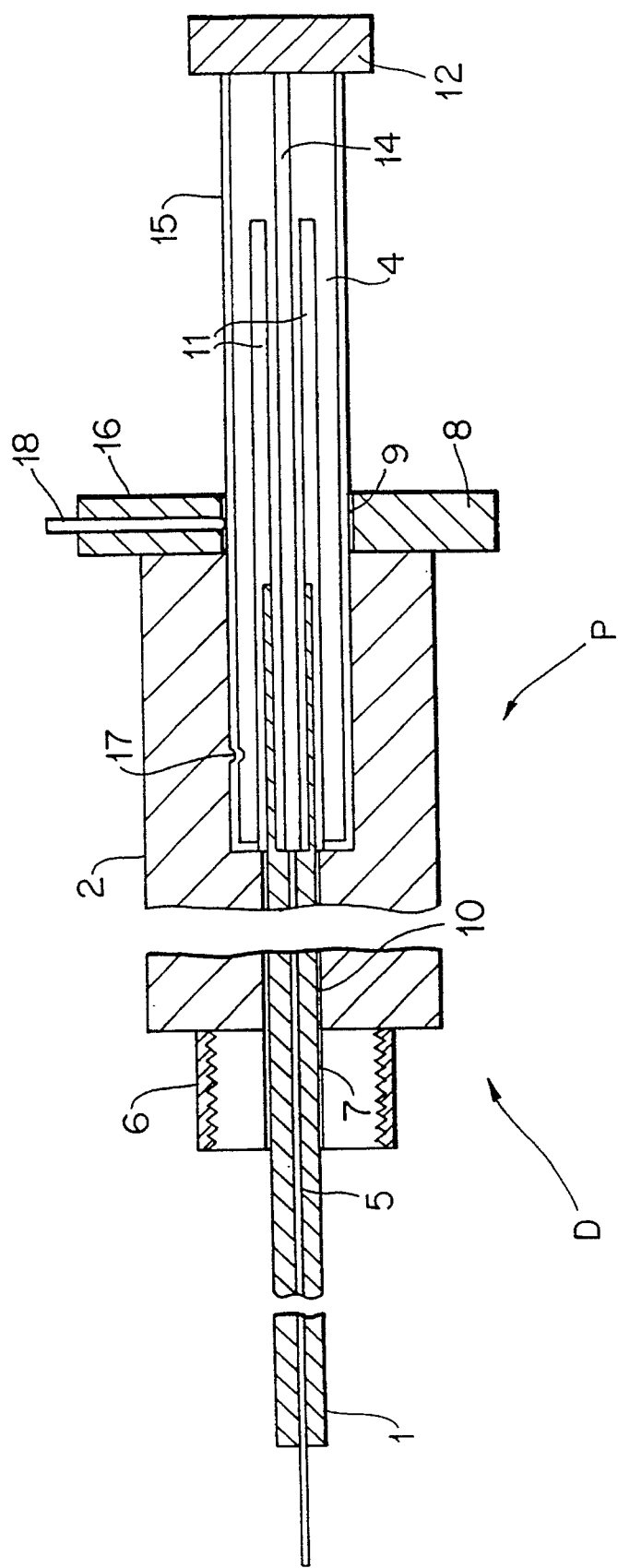

ENDOSCOPIC PUNCTURE NEEDLE DEVICE

The present invention relates to an endoscopic puncture needle device comprising: an elastic catheter introducible into an instrument channel of an endoscope; a flexible hollow puncture needle extending through the catheter; a cylindrical handle casing extending in the longitudinal direction of the hollow puncture needle, the proximal end of the catheter being connected to the distal end of the casing; and a hollow rod connected to the proximal end of the hollow puncture needle, for reciprocating the hollow puncture needle within the catheter, said hollow rod being mounted in the handle casing coaxially with the proximal end of the catheter and displaceably in the longitudinal direction such that the distal end of the hollow needle can be driven out of the catheter in the distal direction by displacing the hollow rod in the casing.

Such a known medical device is used in the process of endoscopic punctures for diagnostic or therapeutic purposes, in particular for the so-called FNA (fine needle aspiration) which involves the aspiration of liquid, solid or gaseous matter from natural or pathologic hollows, or from organs, of the human body. In so doing, the catheter of the device containing the hollow puncture needle is introduced into the instrument channel of an endoscope after the anatomic characteristics of the patient have been determined with the help of the endoscope and, as the case may be, an ultrasonic probe; after the instrument channel and the catheter arranged therein have been positioned as required, the needle is driven out of the catheter by means of the hollow rod such as to puncture the patient's inner organ to be examined. Then, the matter present in this organ, for example liquid matter, can be drawn off through the hollow needle and hollow rod connected thereto with the help of a suction device connectable to the proximal end of the hollow rod.

In the process of this treatment, it is very important that the physician performing the treatment be able easily and precisely to sting the hollow needle into the organ under examination and to adjust the puncture depth precisely, and that the needle remain in the organ in the required position, i.e. at the puncture depth set, throughout the treatment process.

The invention solves the problem of providing and developing an endoscopic puncture needle device of the abovementioned type such that the puncture depth of the hollow puncture needle can be adjusted easily and precisely and remains invariable during the whole treatment process.

According to the invention, this object is achieved by the features that the distal end portion of the handle casing is provided with a thread which can be screwed to a threaded hollow pipe socket arranged at the entry of the instrument channel of the endoscope for passing the catheter through said threaded hollow pipe socket.

The proposal of the invention—to fix the handle casing of the puncture needle device to the entry opening of the instrument channel and, thus, to the endoscope after the catheter of the puncture needle device has been inserted in the instrument channel of the endoscope through the threaded hollow pipe socket thereof—achieves the advantage that the catheter is not displaceable longitudinally relative to the instrument channel of the endoscope during the treatment. This means that the positioning of the catheter extending through the instrument channel and, thus, the positioning of the needle arranged in the catheter, is accomplished through the positioning of the instrument channel itself; as a result, both instruments, the endoscope and the puncture needle device, can be set properly, and held in position, by a single positioning operation. In this arrangement, the puncture depth of the hollow needle is exclusively determined by the position of the instrument channel and by the length of the distal end of the hollow needle driven out of the distal end of the catheter with the help of the hollow rod 4. Immobilising the catheter longitudinally in the instrument channel during the treatment avoids the risk that the puncture depth also depends on a freely settable longitudinal position of the puncture needle device relative to the endoscope, which is the case in the conventional puncture needle devices.

While the thread at the distal end portion of the handle casing may be arranged in the form of an external thread mating with an internally threaded pipe socket at the entry of the endoscope, most endoscopes are provided with an externally threaded pipe socket at their entries. Hence, it is preferred according to the invention to arrange the thread as an internal thread adapted to the externally threaded pipe socket of the endoscope already present.

The design of the puncture needle device according to the invention ensures that the hollow needle can be stung into the organ under examination to a precisely defined extent by displacing the hollow rod in the handle casing once the instrument channel of the endoscope and, thus, the catheter of the puncture needle device have been positioned. In order to be able to set the puncture depth precisely and to monitor it continuously, it is preferred according to the invention that the hollow rod be provided with a scale cooperating with a mark arranged at the handle casing for reading the length of the part of the hollow puncture needle driven out of the catheter in the distal direction. In such an arrangement, the mark may be formed on a transparent longitudinal portion of the circumference of the casing. It is preferred, however, to use, as the mark, the proximal front face of the handle casing through which the hollow rod carrying the scale passes into the handle casing.

It is true that in the puncture needle device according to the invention the proximal end portion of the hollow needle may extend between the proximal end of the catheter and the distal end of the hollow rod without any lateral guidance. However, since the handle casing generally has a great diameter, at least in comparison with that of the hollow needle, to allow easy handling of the puncture needle device, this embodiment entails the risk that the flexible hollow needle might be arcuately bent within the casing when the hollow rod is pushed into the casing; this applies particularly to cases where the hollow needle is to be stung into relatively hard tissue. As a consequence of such bending, the hollow needle would not—or not sufficiently—penetrate the organ under examination, and the scale would not indicate the true puncture depth. Moreover, the hollow needle might become stuck in the handle casing.

According to the invention, it is preferred therefore that a longitudinally extending guide pipe facing the proximal end of the catheter be arranged within the handle casing for guiding the longitudinal portion of the hollow puncture needle between the distal end of the handle casing and the distal end of the hollow rod, the hollow rod and the guide pipe being telescopically displaceable into one another.

Preferably, the guide pipe in the handle casing is formed as an extension of the catheter and has a diameter substantially corresponding to that of the catheter so that the hollow needle is optimally guided in the longitudinal direction even at its proximal end portion to avoid arcuate bending of the needle. If the inner diameter of the guide pipe is considerably greater than the inner diameter of the catheter, the hollow rod can be designed such as to be telescopically insertable in the guide pipe. If, on the other hand, the outer diameter of the hollow rod is greater than the inner diameter of the guide pipe, an axially extending annular groove may be formed in the hollow rod, into which the guide pipe can enter when the hollow rod is pushed into the handle casing.

It is also possible, however, to provide the distal end of the hollow rod with a longitudinally extending pipe socket having its inner diameter adapted to the outer diameter of the guide pipe, resulting in the guide pipe being displaced in said pipe socket when the hollow rod is pushed into the handle casing. This latter embodiment may be employed in particular for applying smaller puncture depths, as in this case the whole length of the handle casing need not be available for the displacement of the hollow rod.

In order to prevent any undesired puncture by the hollow needle, for instance during the positioning of the distal end of the instrument channel, the hollow needle must be held retracted in the catheter during the positioning process. This can be achieved by pulling the hollow rod out of the handle casing in the proximal direction as far as possible, and by keeping the hollow rod in this maximally extracted position during the positioning process. However, in order to avoid any unintentional puncture by the hollow needle in any event, it is preferred according to the invention that the hollow rod be releasably lockable to the handle casing while the hollow puncture needle is in its retracted position within the catheter.

The invention will be described in greater detail below by means of an exemplary embodiment referred to in the drawing. The drawing figure schematically shows a longitudinal section of the puncture needle device according to an embodiment of the invention.

As apparent from the FIGURE, the puncture needle device according to the invention comprises a catheter 1 made of an elastic material, a cylindrical handle casing 2, a hollow rod 4 axially displaceable in the handle casing 2, and a flexible hollow needle 5.

The handle casing 2 is composed of a distal portion D and a proximal portion P. The distal portion D of handle casing 2 is formed as a pipe socket having an internal thread 6 to enable the handle casing 2 to be screwed to an externally threaded hollow pipe socket of an endoscope (not shown) with the help of the internal thread 6. The distal portion D of handle casing 2 further comprises a hollow pipe element 7 mounted in casing 2 in coaxial relation thereto, for fixing the proximal end of catheter 1.

The proximal portion P of casing 2 has a diameter exceeding that of the distal portion D, thus allowing easy handling of the puncture needle device. The proximal end of casing 2 is closed by a cap 8 provided with an axial aperture 9 therein, through which the hollow rod 4 passes into casing 2; the aperture 9 also serves to guide the hollow rod 4 axially in the casing 2. In the proximal portion P of casing 2, there is also provided a guide pipe 10 extending coaxially with casing 2 and forming an extension of the hollow pipe element 7 in this portion P of casing 2.

The hollow rod 4 is provided with an axially extending annular groove 11 for receiving the guide pipe 10 when the hollow rod 4 is pushed into the casing 2. In addition, a terminal member 12 is releasably mounted on the proximal end of hollow rod 4. A scale 15 is provided on the circumference of hollow rod 4 and cooperates with the outer face of cap 8 to allow the length of the part of hollow rod 4 introduced in casing 2 to be read. A locking groove 17 is arranged in the distal end portion of hollow rod 4, while a transversely extending locking pin 18 biased by a spring (not shown) is provided in cap 8 to releasably engage the locking groove 17 when the hollow rod 4 is retracted from casing 2 to a corresponding extent in the proximal direction.

The hollow needle 5 extends through the catheter 1 and enters the casing 2 through the hollow pipe element 7. The proximal end of hollow needle 5 is secured to the distal end of hollow rod 4 and communicates with an axial bore 14 extending along hollow rod 4. The puncture needle device according to the invention is used as follows. First, the hollow rod 4 is extracted from casing 2 in the proximal direction to such an extent that the locking pin 18 engages the locking groove 17 to lock the hollow rod 4 to casing 2. The catheter 1 is slightly longer than the instrument channel of the endoscope, and the length of the catheter 1 and the length of the hollow needle 5 arranged within the catheter 1 are chosen such that in the engaged position of hollow rod 4, the hollow needle 5 is completely received in the catheter 1.

Next, the catheter 1 of the puncture needle device is completely introduced into the instrument channel of the endoscope through the central opening in the externally threaded hollow pipe socket provided at the entry of the endoscope, and the puncture needle device is screwed to the externally threaded pipe socket by means of the internal thread 6. As the catheter 1 is slightly longer than the instrument channel, the catheter 1 protrudes somewhat from the distal end of the instrument channel. The endoscope and the puncture needle device thus mounted on the endoscope will then be positioned as required.

Once the puncture needle device has been positioned, the hollow rod 4 is released from its locked state, and the hollow needle 5 is driven out of the catheter 1 in the distal direction by displacing the hollow rod 4 within casing 2, causing the needle 5 to puncture the organ to be examined. In this operation, the depth of the puncture is determined exclusively by the extent to which the hollow rod 4 is displaced in casing 2 in the distal direction, if the endoscope is kept stationary relative to the patient. Therefore, the puncture depth can be set precisely, and continually monitored during the treatment, with the help of scale 15 arranged on the circumference of hollow rod 4. The scale 15 always indicates the actual puncture depth of needle 5, since the flexible needle 5 is guided in the guide pipe 10 and thus prevented from bending up arcuately in the casing 2 when the hollow rod 4 is displaced in the distal direction.

Finally, the terminal member 12 is detached from the proximal end of hollow rod 4, a suction syringe is connected to said proximal end, and the liquid in the organ under examination, for example, can be drawn out as required through the channel in hollow needle 5 and the axial bore 14 in hollow rod 4. After the examination or treatment has been performed, the hollow needle 5 is retracted into the catheter 1 by displacing the hollow rod 4 in the proximal direction, the hollow rod 4 is again locked to casing 2, and the puncture needle device is withdrawn from the instrument channel by unscrewing the casing 2 from the externally threaded pipe socket of the endoscope.

We claim:

1. An endoscopic puncture needle device comprising: an elastic catheter for insertion into an instrument channel of an endoscope; a flexible hollow puncture needle extending through the catheter; a cylindrical handle casing extending in a longitudinal direction of the hollow puncture needle, a proximal end of the catheter being connected to a distal end of the casing; and a hollow rod connected to proximal end of the hollow puncture needle, for reciprocating the hollow puncture needle within the catheter, said hollow rod being mounted in the handle casing coaxially with the proximal end of the catheter and displaceably in the longitudinal direction such that a distal end of the hollow needle can be driven out of the catheter in a distal direction by displacing the hollow rod in the casing; wherein a distal end portion of the handle casing is provided with a thread for connection to the instrument channel of the endoscope for passing the catheter through the instrument channel.

2. The endoscopic puncture needle device according to claim 1, wherein the thread is internally threaded.

3. The endoscopic puncture needle device according to claim 1 or 2, wherein the hollow rod is provided with a scale cooperating with a mark arranged on the handle casing for reading the length of a part of the hollow puncture needle driven out of the catheter in the distal direction.

4. The endoscopic puncture needle device according to claim 1 or 2, wherein a longitudinally extending guide pipe facing the proximal end of the catheter is arranged within the handle casing for guiding the longitudinal portion of the hollow puncture needle between the distal end of the handle casing and the distal end of the hollow rod, the hollow rod and the guide pipe being telescopically insertable into one another.

5. The endoscopic puncture needle device according to claim 1 or 2, wherein the hollow rod is releasably lockable to the handle casing when the hollow puncture needle is received in the catheter.

6. A puncture needle device for use in connection with an endoscope, the needle device comprising:

a catheter;

a needle contained within the catheter;

a casing connected at a first end to the catheter and having a hollow pipe section coaxial with the catheter for containing a portion of the needle;

a rod mounted at a second end of the casing for slidable movement within the casing in the axial direction, wherein a first end of the needle connects to the rod so that displacement of the rod in the axial direction causes a second end of the needle to withdraw from the catheter; and a cap fixed to the second end of the casing, the cap having locking means for locking the rod to the casing, wherein the locking means includes a locking pin for engaging a locking groove of the rod.

7. A puncture needle device for use in connection with an endoscope, the needle device comprising:

a catheter;

a needle contained within the catheter;

a casing connected at a first end to the catheter and having a hollow pipe section coaxial with the catheter for containing a portion of the needle; and a rod mounted at a second end of the casing for slidable movement within the casing in the axial direction, wherein a first end of the needle connects to the rod so that displacement of the rod in the axial direction causes a second end of the needle to withdraw from the catheter, wherein the casing includes a distal portion at its first end and a proximal portion at its second end, the distal portion having connection means for connecting the needle device to the endoscope.

8. The needle device of claim 7, wherein the connection means includes as internal thread.

* * * * *

UNITED STATES PATENT AND TRADEMARK OFFICE
CERTIFICATE OF CORRECTION

PATENT NO. : 5,601,533
DATED : February 11, 1997
INVENTOR(S) : Soren HANCKE et al.

It is certified that error appears in the above-indentified patent and that said Letters Patent is hereby corrected as shown below:

Claim 1, col. 4, line 64, before "proximal" insert --a--.

Claim 8, col. 6, line 31, change "as" to --an--.

Signed and Sealed this

Twenty-second Day of April, 1997

Attest:

BRUCE LEHMAN

*Commissioner of Patents and Trademarks*

*Attesting Officer*